United States Patent
Chen et al.

(10) Patent No.: US 7,363,091 B1
(45) Date of Patent: Apr. 22, 2008

(54) METHOD OF MOLDING SILICONE ELASTOMER DRUG CARRIER IN AN ENDOCARDIAL LEAD

(75) Inventors: Cole H. Chen, Stevenson Ranch, CA (US); Phong D. Doan, Stevenson Ranch, CA (US); Yougandh Chitre, Valencia, CA (US); John R. Helland, Saugus, CA (US)

(73) Assignee: Pacesetter Inc., Sylmar, CA (US)

( * ) Notice: Subject to any disclaimer, the term of this patent is extended or adjusted under 35 U.S.C. 154(b) by 860 days.

(21) Appl. No.: 10/732,332

(22) Filed: Dec. 9, 2003

Related U.S. Application Data

(63) Continuation-in-part of application No. 09/904,055, filed on Jul. 11, 2001, now abandoned.

(51) Int. Cl.
*A61N 1/05* (2006.01)
(52) U.S. Cl. ..................................... 607/120
(58) Field of Classification Search .............. 607/120, 607/126–128, 130–131; 264/267; 29/857–858
See application file for complete search history.

(56) References Cited

U.S. PATENT DOCUMENTS

| | | | | |
|---|---|---|---|---|
| 4,506,680 A | | 3/1985 | Stokes | 607/120 |
| 4,572,605 A | * | 2/1986 | Hess | 439/585 |
| 4,819,661 A | * | 4/1989 | Heil et al. | 607/127 |
| 4,819,662 A | | 4/1989 | Heil, Jr. et al. | |
| 4,827,940 A | * | 5/1989 | Mayer et al. | 600/375 |
| 5,833,715 A | * | 11/1998 | Vachon et al. | 607/120 |
| 5,837,313 A | * | 11/1998 | Ding et al. | 427/2.21 |
| 5,989,579 A | | 11/1999 | Darougar et al. | 424/427 |
| 6,129,752 A | * | 10/2000 | Neubauer et al. | 607/127 |
| 6,756,048 B1 | * | 6/2004 | Sano et al. | 424/426 |
| 7,174,221 B1 | * | 2/2007 | Chen et al. | 607/120 |
| 2003/0028231 A1 | * | 2/2003 | Partridge et al. | 607/120 |

OTHER PUBLICATIONS

NonFinal Office Action, mailed Aug. 13, 2003: Parent U.S. Appl. No. 09/904,055.
NonFinal Office Action, mailed Apr. 18, 2006: Related U.S. Appl. No. 10/736,082.
Notice of Allowance, mailed Oct. 5, 2006: Related U.S. Appl. No. 10/736,082.

* cited by examiner

*Primary Examiner*—Kennedy J. Schaetzle
*Assistant Examiner*—Jessica L. Reidel

(57) ABSTRACT

A drug-eluting endocardial lead and method of manufacture. The silicone elastomer of the present invention is ideally suited to a manufacturing environment due to its extended pot life and decreased curing time. A preferred silicone elastomer is comprised of a multi-part mixture having at least a base portion and a curing portion. Additionally, since curing does not begin until the base and curing portions are combined, the mixing can be physically undertaken closer to the location of the endocardial lead and the curing "clock" does not start until the mixing occurs and external heat is applied. Since the silicone elastomer formed by base and curing components have improved the pot life and curing characteristics, the mixture is suitable for mixing with a steroid and then dispensing into an endocardial lead tip thus eliminating current design limitations imposed by current art while concomitantly minimizing manufacturing costs.

5 Claims, 13 Drawing Sheets

METHOD OF MOLDING SILICONE ELASTOMER DRUG CARRIER IN AN ENDOCARDIAL LEAD

CROSS-REFERENCE TO RELATED APPLICATIONS

This application is a continuation-in-part of U.S. patent application Ser. No. 09/904,055, filed Jul. 11, 2001, titled "APPARATUS USING A SILICONE ELASTOMER AS A DRUG CARRIER IN A DRUG-ELUTING ENDOCARDIAL LEAD AND METHOD OF MANUFACTURE," now abandoned, and is related to U.S. patent application Ser. No. 10/736,082, filed Dec. 12, 2003, titled "METHOD OF MANUFACTURING DRUG-ELUTING ENDOCARDIAL LEAD UTILIZING SILICONE ELASTOMER AS A DRUG CARRIER," now U.S. Pat. No. 7,174,221.

FIELD OF THE INVENTION

The invention generally relates to implantable cardiac leads for use with devices such as pacemakers and implantable cardioverter/defibrillators (ICDs), and in particular, to such leads that controllably release a drug or steroid at the site of implantation of the lead's tip electrode.

BACKGROUND OF THE INVENTION

A dysrhythmia is an abnormal heart beat pattern. One example of a dysrhythmia is a bradycardia wherein the heart beats at an abnormally slow rate or where significant pauses occur between consecutive beats. Other examples of dysrhythmias include tachyarrhythmias where the heart beats at an abnormally fast rate, e.g., atrial tachycardia where one or more atria of the heart beat abnormally fast. It is well known to treat such dysrhythmias with a pacemaker, an implantable cardiac defibrillator (ICD), or the like which delivers electrical stimulation pulses through one or more electrodes proximate to the distal end of one or more leads implanted within a patient's heart, i.e., endocardial leads. Many types of endocardial leads are known but they generally fit into two broad categories, passive fixation leads that use tines or the like to affix to the trabeculae in the patient's heart and active fixation leads that typically have a screw-in helix that screws into the myocardium. In either case, the mechanical trauma of implanting the endocardial lead will generally result in some degree of inflammation due to, among other things, foreign body reaction that can adversely affect the primary purpose of the implantation, that being to cause the heart tissue to contract by applying electrical stimulating pulses to the heart tissue under the control of the pacemaker. The ability of a pacemaker/ICD to stimulate the heart tissue depends upon overcoming a cardiac pacing threshold. A threshold value is related to the minimum amount of energy contained in a stimulation pulse known amplitude and duration that is capable of stimulating the heart tissue. Typically, the threshold energy value following implantation, i.e., the acute stimulation threshold, is generally higher and decreases during the first few weeks after implant to a more stable chronic stimulation threshold value. It is well known that an endocardial lead can be made to elute a steroid, e.g., dexamethasone sodium phosphate or glucocorticosteroid, to reduce the amount of inflammation resulting from the implant and thus improve the capability of the pacemaker to stimulate the cardiac tissue with a decreased amount of energy, a limited resource in an implanted device. Accordingly, the battery life and the time between implants of a pacemaker/ICD will normally be extended.

Typically, the steroid is eluted from an endocardial lead electrode that contains a monolithic controlled release device (MCRD), in the form of a plug that is made of a mixture of a steroid, e.g., dexamethansone sodium phosphate, or equivalent, and a medical adhesive as a carrier for the steroid. The currently known and used medical adhesive/steroid combinations have limitations that add to manufacturing costs. Typically, the pot life, i.e., the time before the viscosity of the combination makes it difficult to handle (e.g., dispense, inject or spread), is relatively short, e.g., only about 10 minutes. Thus, the pot life limits the capability to mass-produce leads by dispensing or injecting the mixture into a completed or partially completed lead. In contrast, the curing time is typically relatively long, e.g., up to 24 hours. Accordingly, to accommodate for these characteristics, monolithic controlled release device (MCRD) plugs are typically manufactured outside the lead and inserted into the lead as an additional manufacturing step. To manufacture these plugs, a mixture is formed and rapidly (within the pot life limitation) spread over and into multiple cavities in a mold. Typically, the mixture is then cured in an oven at an elevated temperature, e.g., 50° C., for 2 hours and then air cured for an additional 8 hours. After curing is completed, e.g., 10 hours later, the cured plugs are extracted from the mold and subsequently inserted into the partially manufactured lead. This process typically results in a substantial waste of the steroid mixture (the portion that is not actually inserted into the mold cavities) as well as increasing manufacturing delays (due to the curing time), production steps, and the costs associated with each of these deficiencies. Therefore, it is very desirable to have a composition and process for forming a monolithic controlled release device (MCRD) that reduces these material and production costs. Accordingly, the present invention is directed to remedying the deficiencies of the prior art.

SUMMARY OF THE INVENTION

The present invention relates to a drug-eluting endocardial lead that includes a drug dispenser at the lead's distal tip. The drug to be dispensed is intended to significantly reduce cardiac tissue inflammation at the distal tip's implant site. The drug includes a steroid and is mixed with a silicone elastomer to facilitate manufacture of the lead, especially during application of the drug to the lead. The drug carriers of the prior art typically include a medical adhesive that begins to cure as soon as it is exposed to air and has a relatively short pot life and relatively long curing time. The silicone elastomer of the present invention is more ideally suited to a manufacturing environment due to its extended pot life and decreased curing time. A preferred silicone elastomer comprises a multi-part mixture having at least a base portion and a curing portion. Additionally, since curing does not begin until the base and curing portions are combined, i.e., mixed, the mixing can be physically undertaken at the location of final assembly of the lead and the curing time "clock" does not start until the mixing occurs. Since the silicone elastomer formed by the base and curing components has improved pot life and curing characteristics, this mixture is suitable for mixing with a steroid and insertion into an endocardial lead, with the advantage of minimizing manufacturing costs.

A preferred monolithic controlled release device (MCRD) mixture for use in a drug-eluting endocardial lead to facilitate the controlled release of a drug to cardiac tissue comprises a mixture of a drug component that reduces inflammation of cardiac tissue and a silicone elastomer for carrying the drug component, wherein the silicone elastomer is comprised of a base component and a curing component.

In a further aspect of the present invention, the drug component includes a steroid, e.g., dexamethasone sodium phosphate, or equivalent. In a still further aspect of the present invention, the drug component is formed by mixing the drug, such as dexamethasone sodium phosphate, with a wetting fluid such as silicone fluid prior to mixing with the silicone elastomer to facilitate mixing.

A preferred method for forming a monolithic controlled release device (MCRD) mixture for use in a drug-eluting endocardial lead comprises the steps of (1) forming a mixture of a drug and a silicone elastomer for carrying the drug, wherein the mixture is comprised of at least three components, a base component and a curing component for forming the silicone elastomer and a third component containing the drug to be released to the cardiac tissue, (2) dispensing the mixture into a portion of the endocardial lead, and (3) allowing the mixture to cure in place in the endocardial lead. In a further aspect of the preferred method, the curing time of the mixture is decreased by elevating the temperature of the mixture to at least 55° C. In a still further aspect of the preferred method, the third component is formed by mixing the drug, e.g., dexamethansone sodium phosphate, with a silicone fluid to facilitate mixing with the base and curing components, which form the silicone elastomer.

Other aspects, features, and advantages of the invention will be apparent from the detailed description, which follows in combination with the attached drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
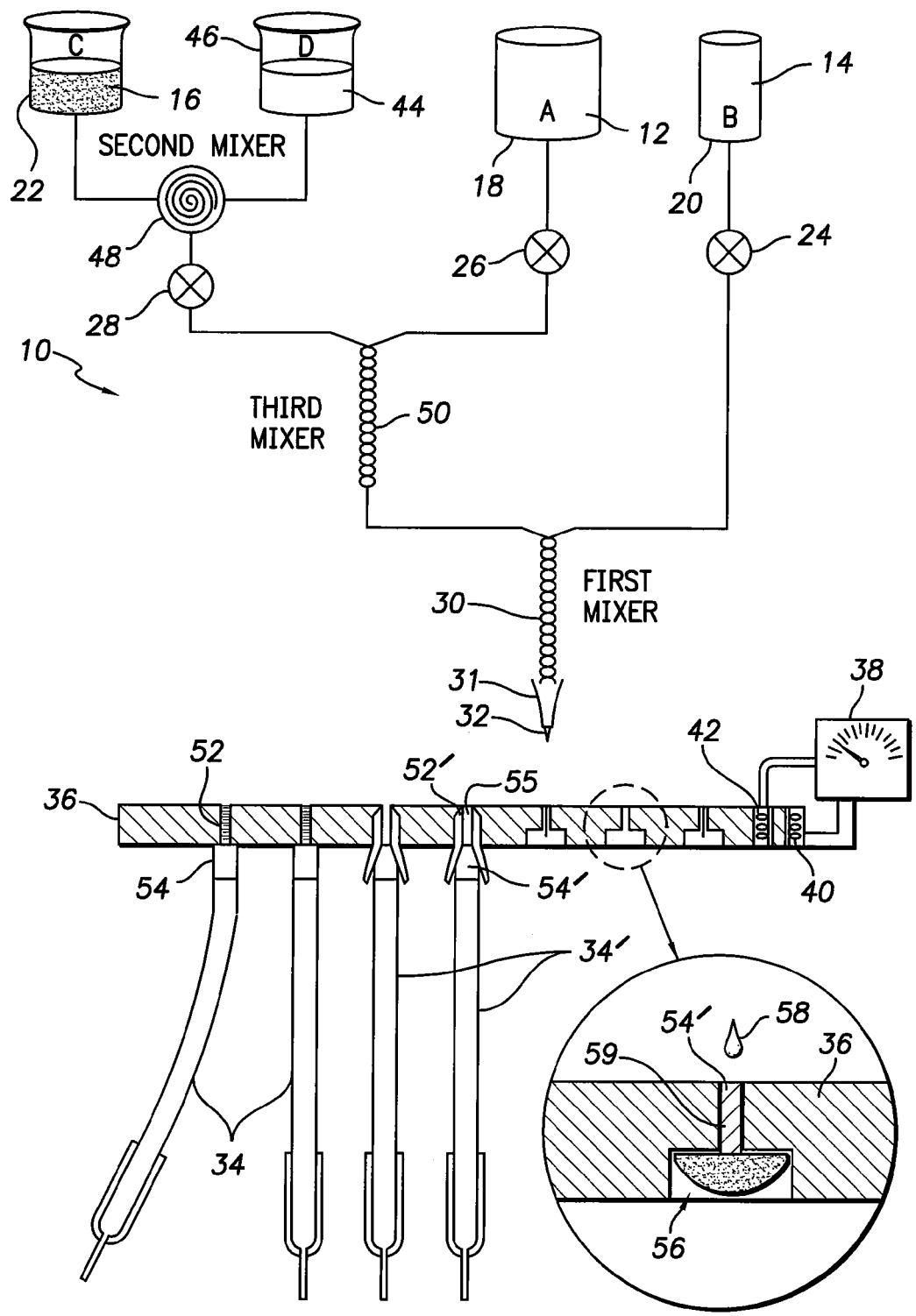
FIG. 1 shows a simplified diagram of the apparatus of the present invention for forming a mixture of a drug, e.g., a steroid, and a silicone elastomer and subsequently dispensing the mixture into a plurality of endocardial leads.

FIG. 1 shows a simplified diagram of the apparatus 10 of the present invention for forming a mixture of a drug, e.g., a steroid, and a silicone elastomer and subsequently dispensing the mixture into a plurality of endocardial leads. Although not shown in detail, the leads 34 and 34' illustrated in FIG. 1 represent implantable cardiac pacing leads, such as endocardial leads well known in the art. As was previously mentioned and also known in the art, upon implant of the lead in the heart, the heart tissue in contact with the lead's distal tip electrode may become inflamed. Heretofore, many attempts have been made to abate the inflammation at the implant site immediately upon implant. These attempts include placing a monolithic controlled release device (hereinafter just "MCRD") mixture in the lead's tip electrode that comes in contact with the cardiac tissue. The efficacy of such MCRD mixtures is of course dependent upon the constituent parts or ingredients comprising the MCRD. The present invention attempts to greatly improve the efficacy of inflammation-reducing drugs with a new compound and method of manufacture that is intended, among other things, to be used in conventional cardiac pacing leads. Each of the leads contemplated for use with the present invention includes a chamber for housing a drug dispensing means, either in the form of a MCRD containing plug or a porous electrode at the lead's distal tip.

The silicone elastomer contemplated for the present invention is formed by mixing and curing multiple components, including at least a base component 12 and a curing component 14. This silicone elastomer is used as a carrier for a drug 16, which is concurrently mixed with the base 12 and curing 14 components. Initially, the base component 12 is loaded into container A 18, the curing component 14 is loaded into container B 20 and the drug 16 is loaded into container C 22. The three components are fed, preferably with the assistance of pumps 24, 26, 28 to a first mixer 30, e.g., a static mixer, where they are combined into a drug/carrier mixture 31, i.e., a monolithic controlled release device (MCRD) mixture. (The mixing process can be further improved with the use of additional components, as discussed further below.) The MCRD mixture 31 (in a pourable form, e.g., 0-2000 poise, until the curing process completes) is then fed into a suitable dispenser 32, such as a needle or equivalent, from which it is dispensed, either by injection or by forming droplets of the mixture into the distal end of an endocardial lead 34. Due to the large pot life, e.g., 1 hour or more, the mixture may be dispensed into a plurality of such leads 34. Accordingly, a plurality of leads 34 may be held by a curing jig 36 (described further below) and the dispenser 32 (or optionally the whole apparatus 10) may be repositioned so that the MCRD mixture 31 can be dispensed into a plurality of leads 34 within the pot life time. Alternatively, one of ordinary skill in the art will readily recognize that the curing jig 36 may be repositioned relative to the dispenser 32 to accomplish the same function. This repositioning can be done via computer numerical control (CNC) type means (not shown) well known in the art, e.g., servo motors, stepper motors, hydraulics, pneumatics, etc.

Once the MCRD mixture 31 has been formed and dispensed, the curing process begins. If left at room temperature, the curing process would take approximately 24 hours. However, elevating the temperature of the MCRD mixture 31 will significantly decrease the curing time and, accordingly, the manufacturing process time. Preferably, the temperature of the MCRD mixture 31 is elevated by heating at least the distal end of the leads 34 to a temperature between 40° C. and 75° C., preferably about 55° C. At the preferred temperature a curing time of approximately 2 hours is anticipated, while at 65° C., the curing time can be further decreased to approximately 1 hour.

To elevate the temperature, a heater controller 38 is used to heat the curing jig 36 (preferably metallic) via a heater 40 and preferably under feedback control of a temperature sensor 42. The operation of such a heater controller 38, e.g., a pulse interval derivative (PID) controller, is well known in the art. Depending upon the selected curing temperature, the MCRD mixture 31 is cured within the endocardial lead in approximately 1 to 2 hours.

In a preferred variation of the aforedescribed process, a wetting fluid 44, placed in container D 46, is premixed with drug 16 (typically in a powder form) by a second mixer 48 to form a premixed fluid drug component that will mix easier with the base 12 and curing 14 components in the first mixer 30. Additionally, it is preferred that this premixed fluid drug component be fed via pump 28 to a third mixer 50, e.g., a static mixer, where it is mixed with the base component 12 before the curing component 14 is mixed in at the first mixer 30.

Apparatus 10 may be used with active fixation leads 34 or may be used with passive fixation leads lead 34'. In the case of the active fixation leads 34, the dispenser 32 is repositioned relative to each lead 34 and the MCRD mixture 31 is either injected or droplets are dripped into the distal tip 52 of the lead 34 and cured in a chamber 54. In the case of a passive fixation lead 34', the MCRD mixture is preferably injected, e.g., via a syringe type nozzle at the end of the dispenser 32 into a chamber 54' through the distal tip 52' of each lead 34'. The MCRD mixture 31 is then cured in the chamber 54'. Alternatively, a plurality of electrode tip portions 56, e.g., ones with sintered porous tips, may be positioned in the curing jig 36 and droplets 58 of the MCRD mixture can be dripped into the backside of the electrode tip 56 and cured. Following curing, the distal electrode tip 56 may be attached, e.g., welded, to the rest of the lead 34' via conventional means. In each of these cases the MCRD mixture 31 cures into a plug 59 within the chamber 54' and thus does not require a separate manufacturing insertion step as is typically found in the prior art. Furthermore, there is little waste and many such leads can be manufactured in a single operation. Accordingly, the material and manufacturing costs are reduced from that typically found in the prior art.

Various materials can be used in the above process. The currently preferred combinations (Drug 16 is dexamethasone sodium phosphate in each of these cases) are described below:

1. From Dow Corning:

| Base Component 12 | Curing Component 14 | Fluid 44 |
|---|---|---|
| MDX4-4210 (dimethylsiloxane polymer and a reinforcing silica) | Platinum catalyst 10:1 by weight | 360 Medical Fluid colorless and odorless polydimethyxiloxane fluid |

2. From Nusil:

| Base Component 12 | Curing Component 14 | Fluid 44 |
|---|---|---|
| MED-4211 or MED-4210 | Platinum catalyst 10:1 by weight | MED 360 dimethylpolymer |

3. From Applied Silicone:

| Base Component 12 | Curing Component 14 | Fluid 44 |
|---|---|---|
| 40072 or 40029 or 40082 | Platinum catalyst 10:1 by weight | 40047 or 40073 or 40074 or 40104 or 40098 medical grade MDM silicone fluid |

Figure 2:
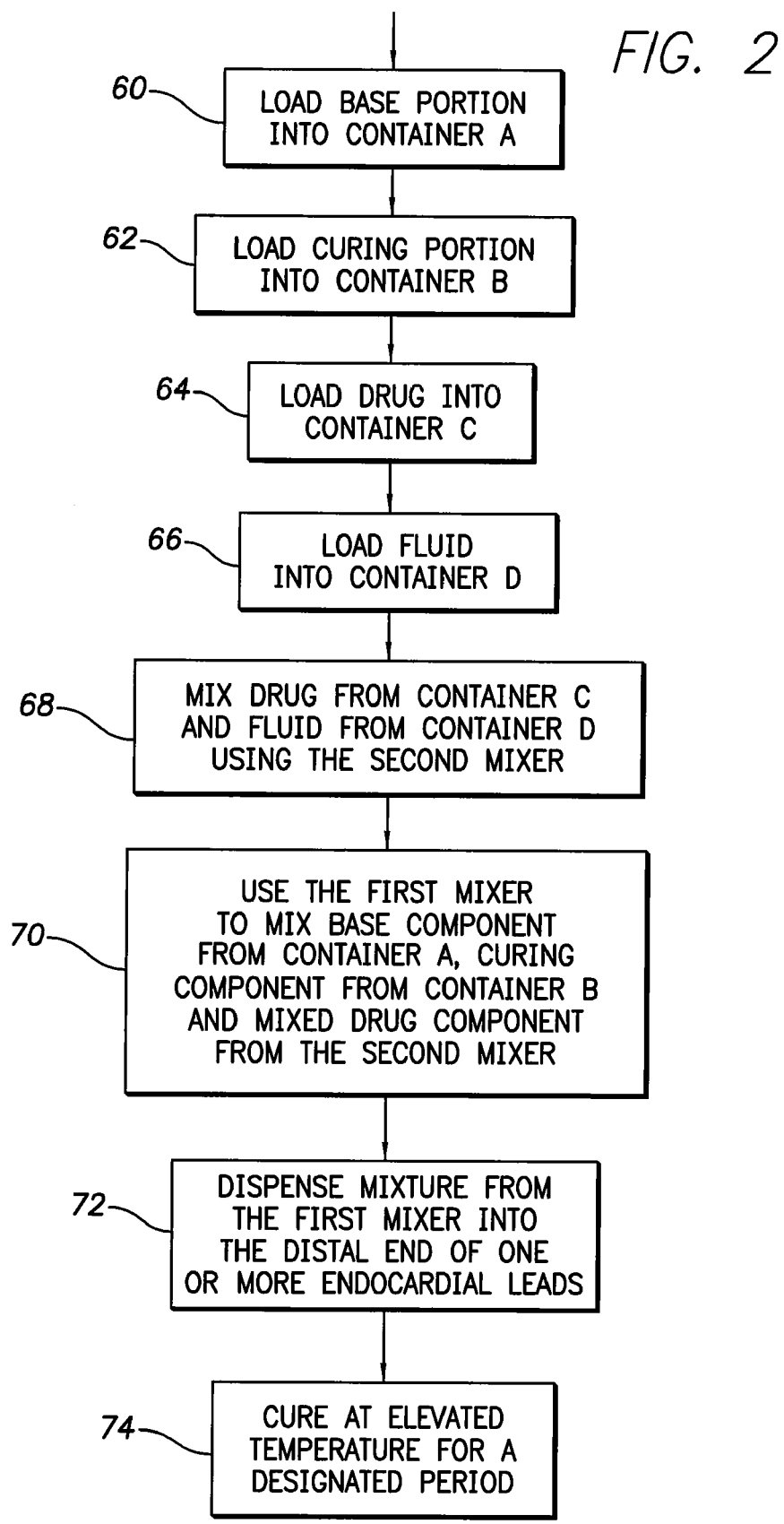
FIG. 2 shows a simplified flow chart of the process used in forming, dispensing and curing the drug-eluting mixture into an endocardial lead.

FIG. 2 shows a simplified flow chart of the process used in forming, dispensing and curing the MCRD mixture into an endocardial lead 34. Initially in steps 60, 62, 64 and 66, containers 18, 20, 22 and 46 are filled with the base component 12, the curing component 14, the drug component 16, and the fluid component 44, respectively. Next, in step 68, the drug and fluid, e.g., wetting fluid, are mixed using the second mixer 48. This wetted drug mixture is then mixed in step 70 with the base 12 and curing 14 components using the first mixer 30 and dispensed in step 72 used the dispenser 32. Optionally, the wetted drug mixture is first mixed with the base component 12 using the third mixer 50 before mixing with the curing component in the first mixer 30. Finally, the temperature of the dispensed MCRD mixture 31 is elevated in step 74 to reduce the curing time.

Figure 3:
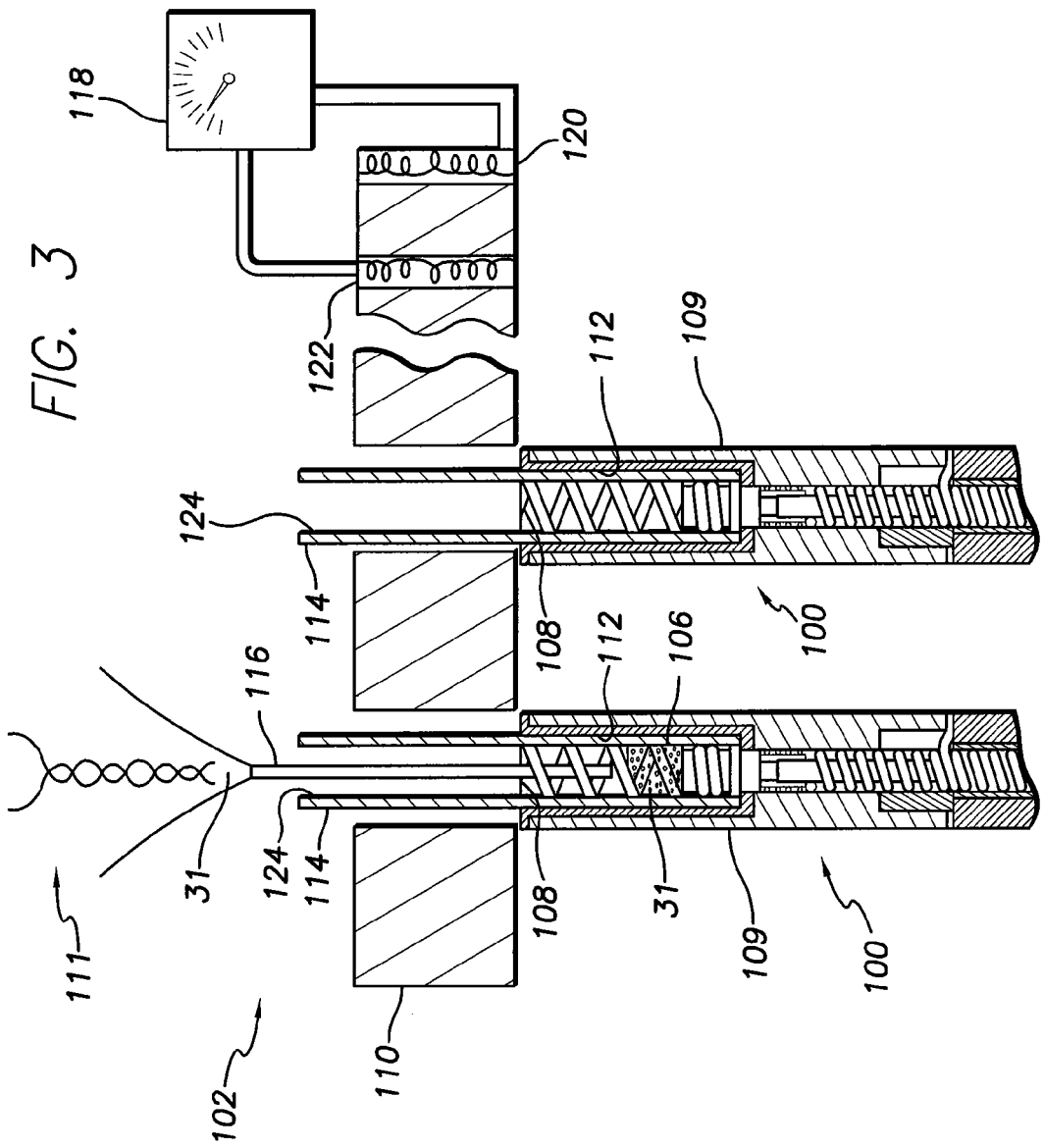
FIG. 3 shows a longitudinal section of a distal end portion of an active fixation lead and a plug forming apparatus in accordance with an exemplary embodiment.
Figure 4:
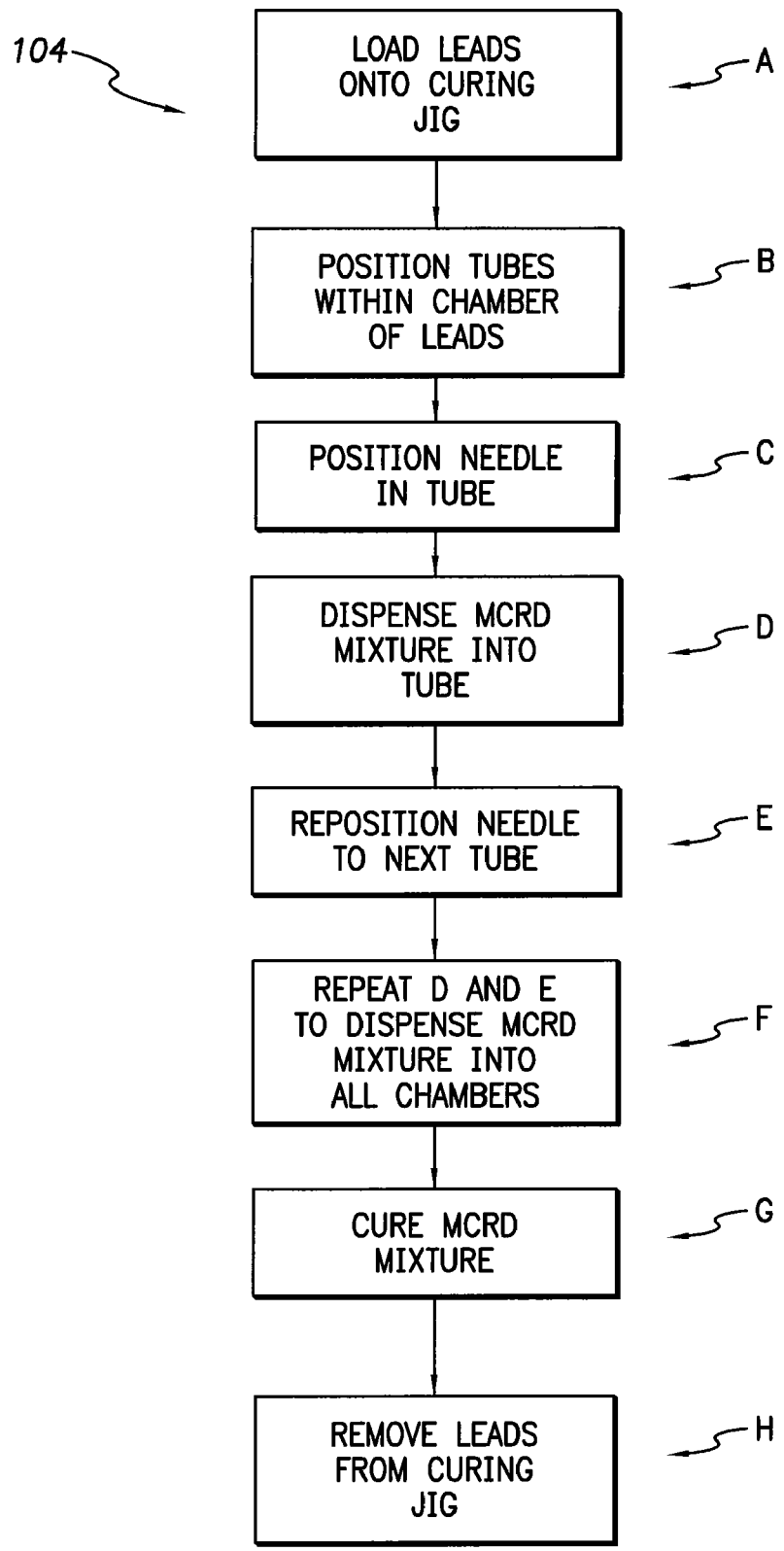
FIG. 4 is a simplified flow chart showing the process for forming a drug-eluting plug disposed within a chamber of the active fixation lead of FIG. 3.

FIG. 3 shows an exemplary active fixation lead 100 and a plug forming apparatus 102, and FIG. 4 is a flowchart 104 showing process A through H for forming a plug 106 molded to a screw-in helix 108 disposed at a distal portion of the active fixation lead 100. A plurality of active fixation leads 100, which have lead bodies 109, may be held by a curing jig 110. A dispenser 111 may be positioned so that the MCRD mixture 31 can be dispensed into the plurality of active fixation leads 100 within the pot life time. Prior to dispensing the MCRD mixture 31 into a chamber 112 of the active fixation lead 100, a mold is inserted into the chamber 112 to temporarily house the MCRD mixture 31. In the exemplary embodiment shown in FIG. 3, the mold is a tube 114 having an outer diameter sized to slidingly fit within the chamber 112 of the active fixation lead 100. The tube 114 has an inner diameter appropriately sized to receive the screw-in helix 108.

The dispenser 109 is provided with a needle 116, and the needle 116 is inserted within the tube 114 to allow the MCRD mixture 31 to be selectively dispensed onto a proximal portion of the screw-in helix 108 such that a distal portion of the screw-in helix 108 is not covered with the MCRD mixture 31 to ensure proper electrical contact of the screw-in helix 108 with the heart tissue. After the proper amount of MCRD mixture 31 is dispensed into the chamber 112, the needle 116 is retracted from the chamber 112. The needle 116 is then repositioned to the next tube 114 and the MCRD mixture 31 is dispensed. Repositioning of the needle 116 and dispensing of the MCRD mixture 31 is repeated for the remaining fixation leads 100. A heat controller 118 is used to heat the curing jig 110 via a heater and under a feedback control of a temperature sensor 122. After the MCRD mixture 31 has cured into the plug 106, the tube 114 is retracted from the chamber 112. An inner wall 124 of the tube 114 may be coated with a releasing agent to assure trouble-free release of the tube 114 from the plug 106.

Figure 5:
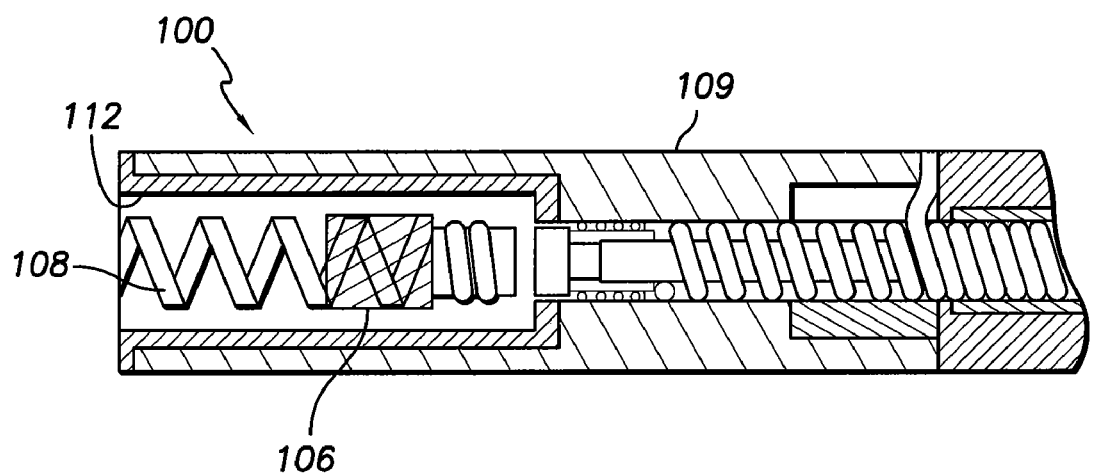
FIG. 5 shows a drug-eluting plug disposed within the chamber of the active fixation lead of FIG. 3.

FIG. 5 shows the plug 106 within the chamber 112 of the active fixation lead of FIG. 3. The plug 106 is secured to the proximal portion of the screw-in helix 108 such that extension and retraction of the screw-In helix 108 relative to the lead body 109 results in the extension and retraction of the plug 106. In the exemplary embodiment, an outer diameter of the plug 106 is substantially the same as the outer coil diameter of the screw-in helix 108.

Figure 6:
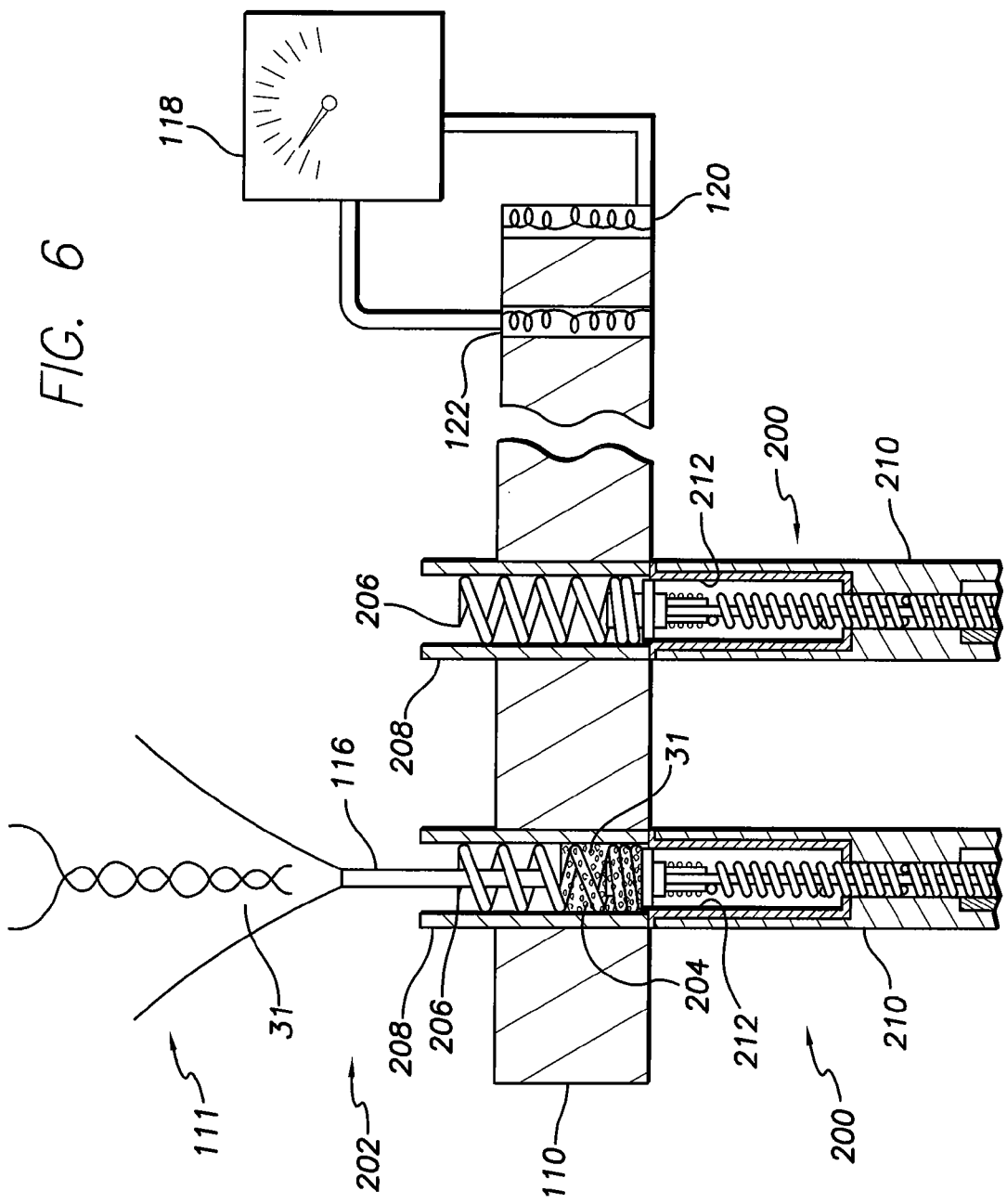
FIG. 6 shows a longitudinal section of a distal end of an active fixation lead and a plug forming apparatus in accordance with another exemplary embodiment.
Figure 7:
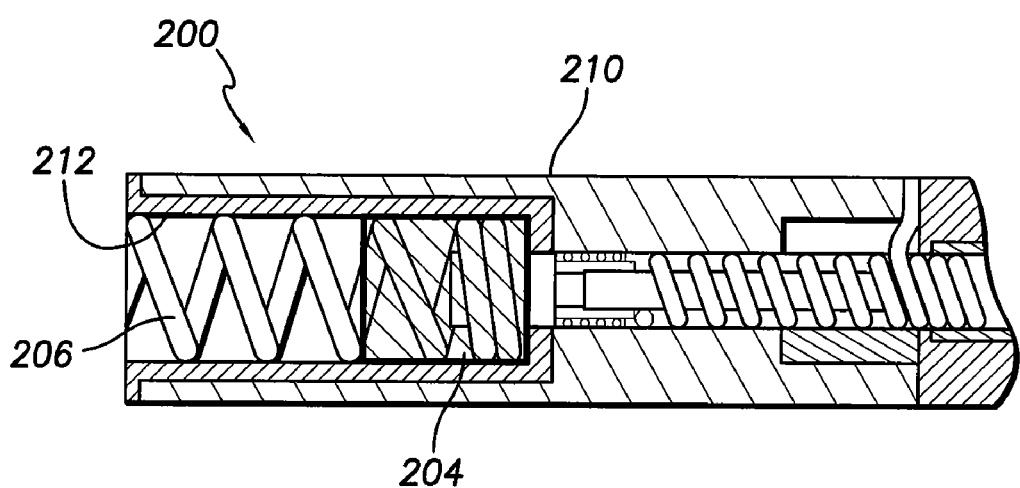
FIG. 7 shows a drug-eluting plug disposed within a chamber of the active fixation lead of FIG. 6.

FIG. 6 shows another exemplary embodiment of an active fixation lead 200 and a plug forming apparatus 202. The process of forming a plug 204 is similar to the embodiment of FIGS. 3-5 with the exception that a screw-in helix 206 is extended during the dispensing of the MCRD mixture 31, and an end of a tube 208 is positioned at a distal end of a lead body 210. By positioning the tube 208 external to the lead body 210, the outer diameter of the plug 204 and the screw-in helix 206 may be dimensioned essentially the same or less than an inner wall diameter of a chamber 212 of the lead body 210. FIG. 7 shows the plug 204 disposed within the chamber 212 of the active fixation lead 200 of FIG. 6.

Figure 8:
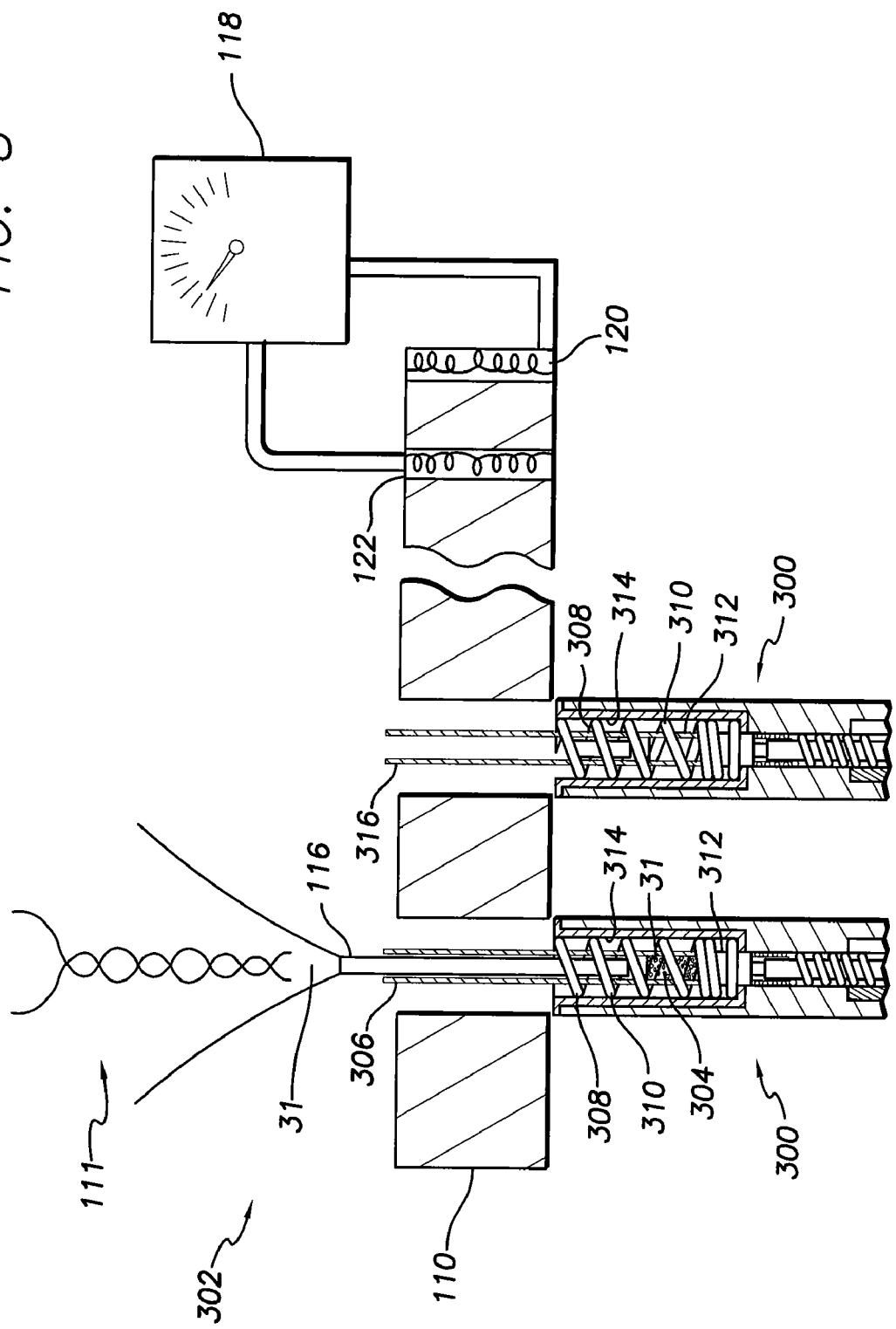
FIG. 8 shows a longitudinal section of a distal end of an active fixation lead and a plug forming apparatus in accordance with still another exemplary embodiment.
Figure 9:
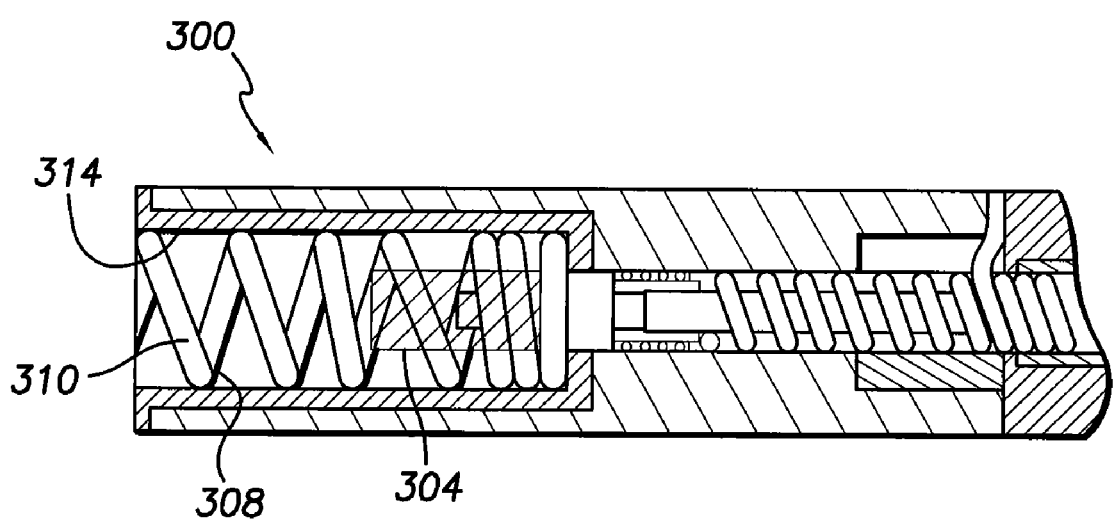
FIG. 9 shows a drug-eluting plug disposed within a chamber of the active fixation lead of FIG. 8.

FIG. 8 shows still another exemplary embodiment of an active fixation lead 300 and a plug forming apparatus 302. The process of forming a plug 304 is similar to the embodiment of FIGS. 3-5 with the exception that a tube 306 is positioned within coils 308 of a screw-in helix 310 such that an outer diameter of the plug 304 is less than an inner coil diameter of the screw-in helix 310 and the plug 304 is molded onto a shaft 312. FIG. 9 shows the plug 304 disposed within a chamber 314 of the active fixation lead 300 of FIG. 8.

Figure 10:
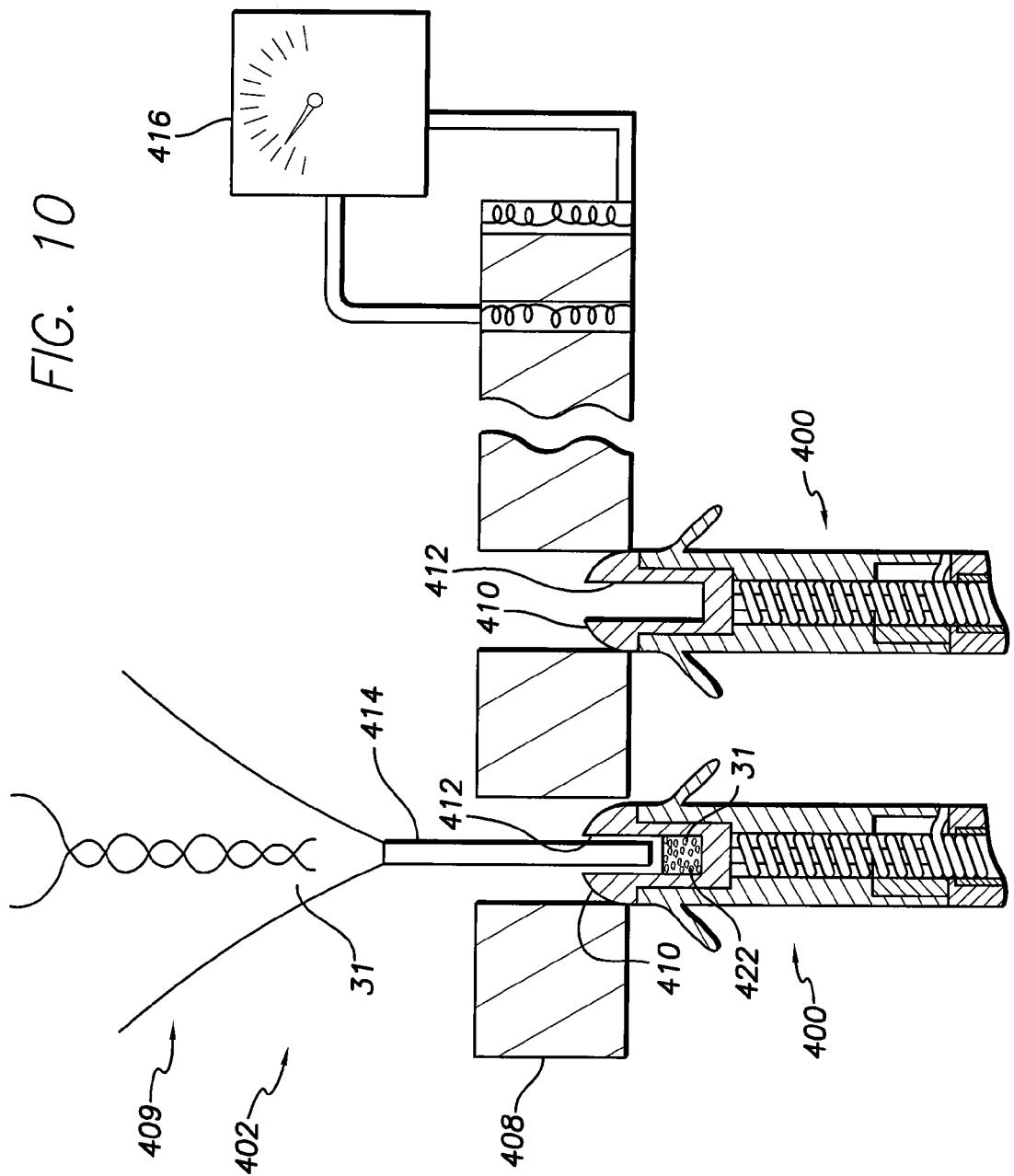
FIG. 10 shows a longitudinal section of a distal end portion of a passive fixation lead and a plug forming apparatus in accordance with an exemplary embodiment.
Figure 11:
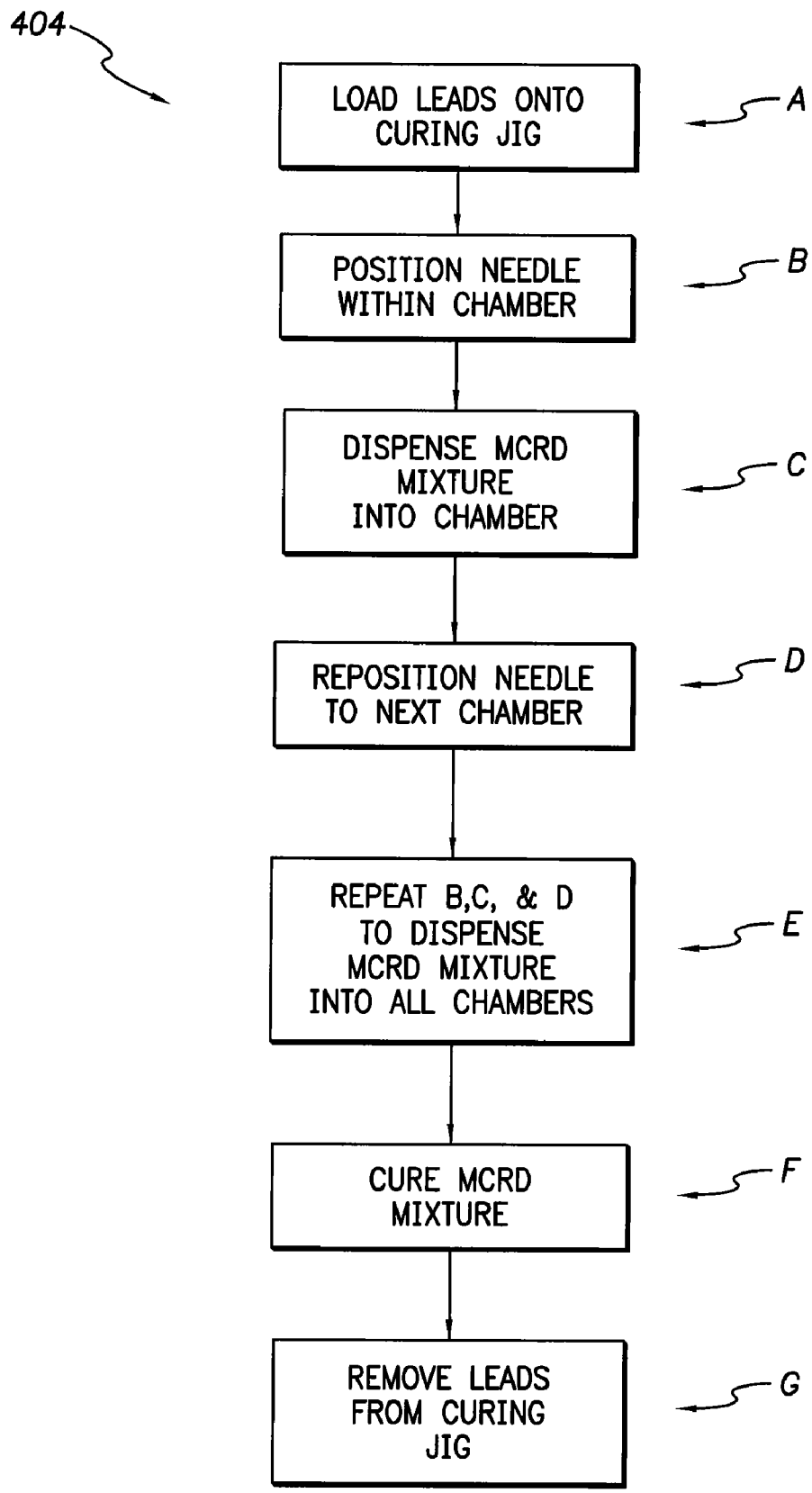
FIG. 11 is a simplified flow chart showing the process for forming a drug-eluting plug disposed within a chamber of the passive fixation lead of FIG. 10.
Figure 12:
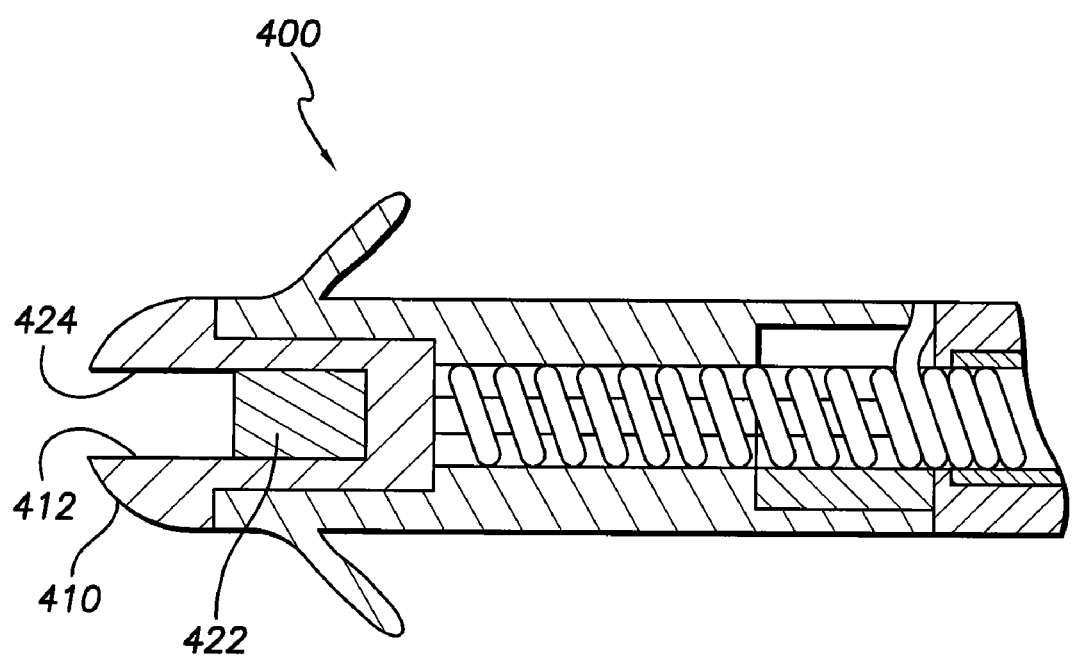
FIG. 12 shows the drug-eluting plug disposed within the chamber of the passive fixation lead of FIG. 10.

FIG. 10 shows an exemplary passive fixation lead 400 and a plug forming apparatus 402, and FIG. 11 is a flowchart 404 showing process A through G for forming a plug 406. As discussed previously with regards to FIG. 1, a plurality of passive fixation leads 400 may be held by a curing jig 408, and a dispenser 409 may be positioned so that the MCRD mixture 31 can be dispensed into the plurality of passive fixation leads 400 within the pot life time. An electrode tip 410 is located at a distal tip of the passive fixation lead 400, and a chamber 412 is disposed within the electrode tip 410. A needle 414 of the dispenser 409 is positioned within the chamber 412 such that the MCRD mixture 31 is dispensed at a proximal portion of the chamber 412. After the proper amount of MCRD mixture 31 is dispensed, the needle 414 is retracted from the chamber 412. A heat controller 416 is used to heat the curing jig 408 via a heater 418 and under a feedback control of a temperature sensor 420 to cure the MCRD mixture into a plug 422. FIG. 12 shows the plug 422 disposed within the chamber 412 of the passive fixation lead 400. The chamber 412 has a bore 424 which serves as a drug-elution path.

Figure 13:
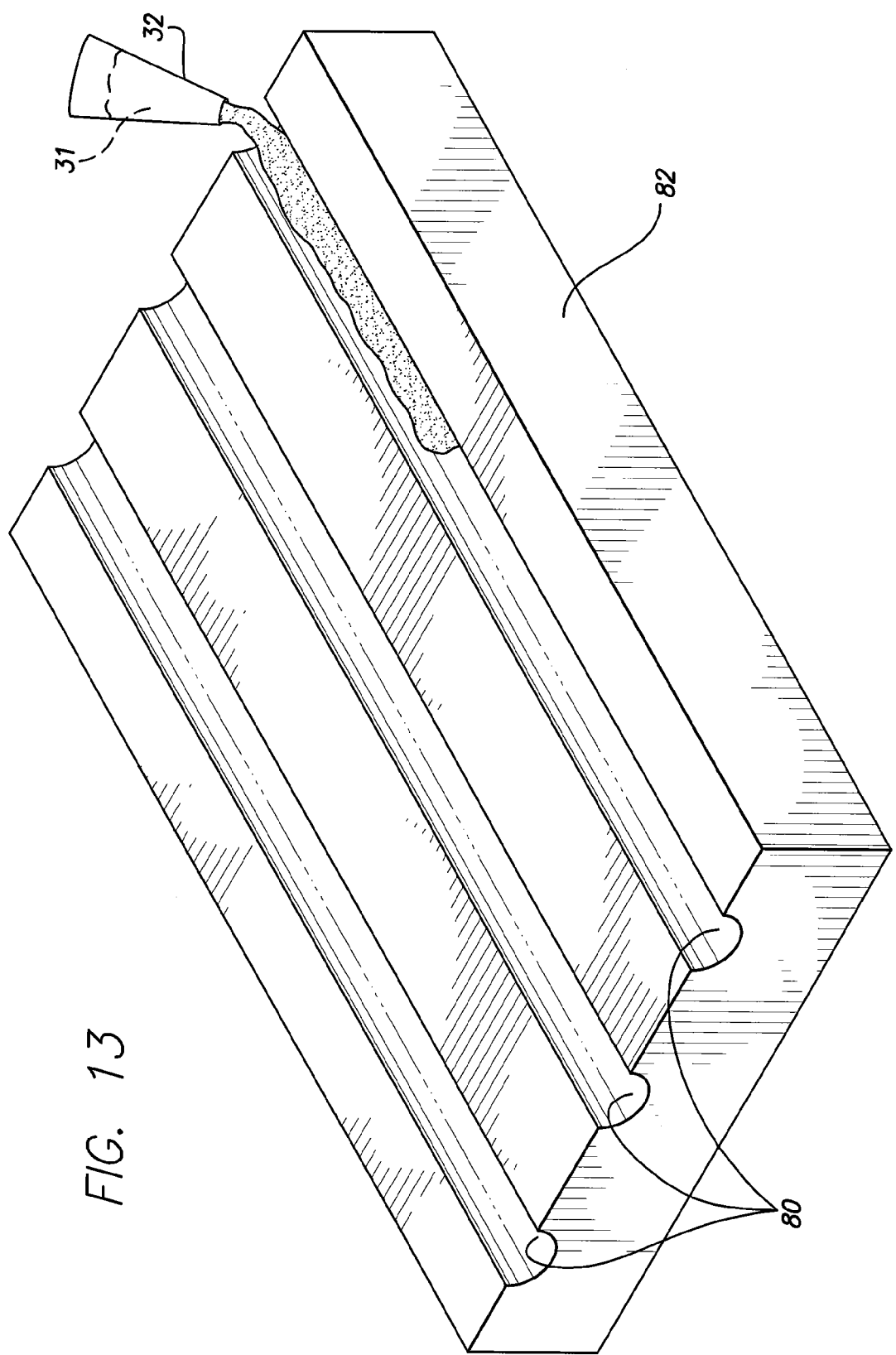
FIG. 13 shows a curing jig used for accepting beads of a mixture of the drug and the silicone elastomer and curing the mixture prior to slicing the cured monolithic controlled release device (MCRD) mixture into drug-eluting plugs for insertion in an endocardial lead.

While the invention has been described by means of specific embodiments and applications thereof, it is understood that numerous modifications and variations could be made thereto by those skilled in the art without departing from the spirit and scope of the invention. For example, while dexamethasone sodium phosphate is the preferred steroid drug to be used in forming the MCRD, other drugs and steroids could also be used, e.g., glucocorticosteroid. Furthermore, while the disclosed composition is particularly suitable for eliminating manufacturing steps, its improved curing properties can also be beneficially used to more quickly generate externally molded plugs for later insertion into endocardial leads. For example as shown in FIG. 13, the dispenser 32 may be used to dispense beads of uncured MCRD material 31 into one or more grooves 80 on a heated curing jig plate 82. Once the beads are cured, the MCRD material may be sliced into plugs and inserted into endocardial leads as in the prior art. However, this process will still be completed in less time and with less waste. Alternatively, any curing jig having a plurality of curing cavities may be used. It is therefore to be understood that within the scope of the claims, the invention may be practiced otherwise than as specifically described herein.

What is claimed is:

1. A method to manufacture a drug-eluting lead comprising:
    positioning a removable mold around a screw-in helix of the drug-eluding lead;
    dispensing a liquid monolithic controlled release device (MCRD) mixture directly into the removable mold and onto a distal portion of the drug-eluting lead;
    curing the liquid MCRD mixture into a drug-eluting plug; and
    removing the removable mold after the MCRD mixture has cured;
    wherein positioning the removable mold around the screw-in helix comprises positioning a distal end of the removable mold within a chamber of the drug-eluding lead, and wherein the chamber houses the screw-in helix when in a retracted position.

2. The method of claim 1, further comprising:
    forming the liquid monolithic controlled release device (MCRD) mixture;
    wherein the forming the liquid MCRD mixture comprises combining an inflammation-reducing drug with a drug carrying silicone elastomer.

3. The method of claim 2, wherein the inflammation-reducing drug is a steroid, and wherein the drug carrying silicone elastomer comprises a platinum catalyst as a curing component and dimethylsiloxane and a reinforcing silica as a base component.

4. The method of claim 1, further comprising:
    dispensing the liquid MCRD mixture onto the screw-in helix;
    wherein the drug-eluting plug is integral with the screw-in helix.

5. A method to manufacture a drug-eluting lead comprising:
    positioning a screw-in helix within a chamber of the drug-eluding lead, a proximal portion of the screw-in helix coupled to a shaft;

positioning a removable mold within an inner coil diameter of the screw-in helix of the drug-eluding lead, wherein a distal portion of the removable mold is positioned at the shaft;

dispensing a liquid monolithic controlled release device (MCRD) mixture directly into the removable mold and onto a distal portion of the drug-eluting lead;

curing the liquid MCRD mixture into a drug-eluting plug; and removing the removable mold after the MCRD mixture has cured;

wherein the drug-eluting plug is integral with the shaft; and wherein the drug-eluting plug is disposed within an inner coil diameter of the screw-in helix.

* * * * *